US006632613B1

(12) United States Patent
Wei et al.

(10) Patent No.: US 6,632,613 B1
(45) Date of Patent: Oct. 14, 2003

(54) COMPOSITIONS AND KITS FOR FLUORESCENCE POLARIZATION ASSAY OF LARGE MOLECULES

(75) Inventors: Ai-Ping Wei, Salt Lake City, UT (US); James N. Herron, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 08/483,500

(22) Filed: Jun. 7, 1995

Related U.S. Application Data

(63) Continuation of application No. 08/164,911, filed on Dec. 9, 1993, now abandoned, which is a continuation-in-part of application No. 08/096,338, filed on Jul. 23, 1993, now Pat. No. 6,482,655, and a continuation-in-part of application No. 08/071,579, filed on Jun. 2, 1993, now abandoned.

(51) Int. Cl.[7] .............................................. G01N 33/53
(52) U.S. Cl. ........................................ 435/7.1; 435/975
(58) Field of Search .................................. 435/7.1, 975

(56) References Cited

U.S. PATENT DOCUMENTS

| | | | |
|---|---|---|---|
| 4,517,290 A | * | 5/1985 | Iwasa et al. |
| 4,681,859 A | | 7/1987 | Kramer |
| 4,833,092 A | | 5/1989 | Geysen |
| 4,879,213 A | * | 11/1989 | Fox et al. |
| 5,070,025 A | | 12/1991 | Klein et al. |
| 5,075,211 A | * | 12/1991 | Cosand et al. |
| 5,143,854 A | * | 9/1992 | Pirrung et al. |
| 5,168,041 A | * | 12/1992 | Bergmann |
| 5,186,897 A | | 2/1993 | Eason et al. |

FOREIGN PATENT DOCUMENTS

| | | | |
|---|---|---|---|
| EP | 0044710 | * | 1/1982 |
| WO | WO 94/27137 | | 11/1994 |

OTHER PUBLICATIONS

Geysen et al, 1987. Strategies for eptioge analysis using peptide synthesis J Immunol Meth 102: 259–274.*
Hunter, 1978, "Radioimmunossay" in *Handbook of Experimental Immunology, vol. 1. Immunochemistry* (D.M. Weir, ed) Blackwell Scientific Publ., Oxford, pp. 14–1, 14.18–14.26.*
Harlowe & Lane "Antibodies A Laboratory Manual" (1988) Cold Spring Harbor Laboratory p. 76.*
Dzgoev et al Biorg. Khim (1993) 19(7): 721.*
Van Erp et al., "Affinity of monoclonal antibodies Interpretation of the positive cooperative nature of anti–hCg/hCG interactions", *J. Immunol. Methods*, 140:235–241, 1991.

Wei et al., "Use of Synthetic Peptides as Tracer Antigens in Fluorescence Polarization Immunoassays of High Molecular Weight Analytes", *Analytical Chemistry*, vol. 65, No. 23, Dec. 1, 1993, pp. 3372–3377.
Weir, D.M., "vol. 1 Immunochemistry", *Handbook of Experimental Immunology in Three Volumes*, 1978, pp. 14–1, 14–18–14.26.
Bennington, Saunders Dictionary & Encyclopedia of Laboratory Medicine and Technology, pp. 307–308 (1984).
Lu–Steffes et al., "Fluorescence Polarization Immunoassay IV. Determination of Phenytoin and Phenobarbital in Human Serum and Plasma", Clin. Chem., 28(11):2278–2282 (1982).
Tsuruoka, "Fluorescence polarization immunoassay employing immobilized antibody", Biosensors & Bioelectronics, 6:501–505 (1991).
Urios & Citfanova, "Adaptation of Fluorescence Polarization Immunoassay to the Assay of Macromolecules", Analytical Biochemistry, 185:308–312 (1990).
Urios et al., "Immunoassay of the Human Chorionic Gonadotrophin Using Fluorescence Polarization", FEBS Letters, 94(1):54–58 (Oct. 1978).
Watanabe & Miyai, "Fluorescence Polarization Immunoassay Theory and Application", Nonisotopic Immunoassay, 199–209 (Plenum Press, 1988).
Jiskoot et al., "Preparation and application of a fluorescein–labeled peptide for determining the affinity constant of a monoclonal antibody–hapten complex by fluorescence polarization", *Analytical Biochemistry* 196:421–426 (1991).

* cited by examiner

*Primary Examiner*—Mark Navarro
(74) *Attorney, Agent, or Firm*—TraskBritt

(57) ABSTRACT

An improved oligopeptide composition for use in a fluorescent polarization immunoassay for a high molecular weight analyte is disclosed, along with a kit and a method using the composition. The composition comprises an oligopeptide selected by a screening procedure in which a plurality of different oligopeptides having respective amino acid sequences that represent sequential overlapping segments of the analyte amino acid sequence, and a fluorescent label bound thereto. In a preferred embodiment, the oligopeptide has an amino acid sequence which does not form internal disulfide bridges. Such a preferred oligopeptide will generally have no more than one cysteine residue. In a further preferred embodiment, the fluorescent label is tetramethylrhodamine or a cyanine dye. The kit may be packaged with instructions directing a user to prepare an assay solution containing the monoclonal antibody and the oligopeptide in certain respective concentrations. The composition, method and kit are preferably constructed to detect nanomolar concentrations of the analyte.

20 Claims, 6 Drawing Sheets

COMPOSITIONS AND KITS FOR FLUORESCENCE POLARIZATION ASSAY OF LARGE MOLECULES

RELATED APPLICATIONS

This application is a continuation of application Ser. No. 08/164,911, filed Dec. 9, 1993, now abandoned, which is a continuation-in-part of application Ser. No. 08/096,338 filed Jul. 23, 1993, now U.S. Pat. No. 6,482,655 and a continuation-in-part of application Ser. No. 08/071,579 filed Jun. 2, 1993, now abandoned.

BACKGROUND OF THE INVENTION

1. Field

The present invention relates to a fluorogenic homogeneous assay procedure for determination of high molecular weight molecules in solution.

2. State of the Art

A fluorescent molecule is one which, in response to absorption of light in a characteristic frequency range, emits a photon of longer wavelength. When polarized light is used to stimulate the fluorescence, the light emitted by a plurality of such excited fluorescent molecules is often at least partially polarized, since the emitted photons are emitted at a 90° angle with respect to the incident exciting light. This phenomenon is generally termed fluorescence polarization, and can be exploited for quantitation of free vs. analyte-bound fluorescent molecules.

The extent of polarization is a function of several factors including temperature, the rotational mobility of the molecules and solution viscosity. In general, small molecules that rotate rapidly emit light which is less polarized because the emitted light is partially depolarized by the rapid rotation. Very large molecules, however, have limited rotation, which results in a greater degree of polarization.

Fluorescent polarization immunoassays (FPIA or FPI assays) typically use a fluorescently-labelled analyte in conjunction with an antibody which binds the analyte. When the labeled analyte binds to the antibody, the polarization of the fluorescent label increases due to the large hydrodynamic volume of the antigen-antibody conjugate. When unlabelled analyte in a test solution is added to a solution containing the labelled antigen-antibody complex, it competes with the labelled antigen for binding to the antibody. As a result, some of the labelled analyte is displaced into solution, thus decreasing the polarization of the emitted fluorescence. The decrease in polarization occurring upon displacement of labeled analyte is proportional to the amount of unlabeled analyte. The final polarization value may then be used to determine analyte concentration by using a standard curve relating polarization and concentration of unlabelled analyte.

This form of FPI assay has been widely used to determine the concentration of low molecular weight analytes such as drugs and haptens in blood and urine. High molecular weight analytes, however, such as immunoglobulin G (IgG) and human chorionic gonadotrophin (hCG) have been difficult to quantitate with FPIA because the fluorescence polarization value of the free analyte does not differ appreciably from that of the analyte-antibody conjugate. Consequently, the change in polarization as the fluorescently-labelled analyte is displaced by the unlabeled analyte is not sufficient for accurate quantitation.

At least two FPIA methods for measuring high molecular weight antigens exist in the art. U.S. Pat. No. 4,681,859 (Kramer) teaches a method in which a fluorescently labeled small protein or polypeptide is produced that simulates the binding site of a large molecular weight analyte and is capable of binding to the antibody. Because the simulating protein is of relatively low molecular weight, a detectable change in polarization is observed upon its displacement from the antibody by the high molecular weight analyte. The simulator protein of Kramer has the same amino acid sequence as the binding site of the native analyte which binds to the antibody.

Although the method of Kramer may be used to determine the presence of large molecular weight antigens, the accuracy of a quantitation involving the degree of depolarization is more problematic. Factors such as differences in the binding constants between the simulator protein and the native analyte, and the conformation and orientation of the fluorescing compound when the simulator is bound to the antibody, may affect the magnitude of the changes in polarization. Accordingly, the method of Kramer may be improved upon with respect to a quantitative procedure.

U.S. Pat. No. 5,070,025 (Klein et al.) teaches an FPIA process using a fluorescently labeled oligopeptide ("tracer") of 6 to 14 amino acids which is capable of binding to an analyte-specific antibody. The oligopeptide is required to have exactly two cysteine residues which form an intramolecular disulfide bridge. The use of an oligopeptide with a disulfide bridge is typical of early approaches to obtaining an oligopeptide which binds to an antibody with high affinity, in which stabilization of the tertiary configuration of the oligopeptide was deemed necessary. Klein teaches that an otherwise suitable oligopeptide should be altered by appropriate substitutions of amino acids to achieve the result of an oligopeptide which forms a single disulfide bridge in a defined position. Such substitution and the secondary process of causing the bridge to form, is tedious and may affect the fluorescence enhancement and polarization of the labelled oligopeptide when it binds to the antibody. Thus, it is desirable to have an oligopeptide for an FPI assay which does not require stabilization by a disulfide bridge.

Klein et al. further teach that an oligopeptide for an FPI assay should have a molar binding affinity for the antibody which is within a factor of 6 of the binding affinity of the analyte for the antibody. It is often difficult to find oligopeptides whose binding affinity for the antibody is so high compared to the binding affinity of the analyte itself.

Furthermore, the process of Klein is taught to be capable of determining concentrations of insulin on the order of micrograms/milliliter (e.g., micromolar concentrations). However, many analytes are present at concentrations much lower than micrograms per ml, and it would be desirable to be able to detect concentrations as low as nanomolar.

Accordingly, there is a need for improved compositions and methods for fluorescence polarization immunoassay for high molecular weight analytes that provides improved sensitivity and accuracy in quantification. Desirably, an oligopeptide of the composition should be useful even with a binding affinity for the antibody which as much as 100 fold lower than that of the analyte. The method should be rapid, simple and inexpensive to perform, and should be suitable for use in a clinical setting.

SUMMARY OF THE INVENTION

The invention is an improved oligopeptide composition for use in a fluorescent polarization immunoassay for a high molecular weight analyte. The composition comprises a fluorescent label bound to an oligopeptide having an amino acid sequence which does not form internal disulfide bridges, a molecular weight which is less than about 1/500 of the molecular weight of the antibody which binds the analyte in the immunoassay. In a highly preferred embodiment, the composition exhibits an increase in fluorescence upon binding to the antibody. In another embodiment, the oligopeptide has a binding affinity for the antibody of between about 1/10 and 1/10000 of the binding affinity of the analyte for the antibody. In still another embodiment, the oligopeptide is selected by a screening procedure in which a plurality of different oligopeptides having respective amino acid sequences that represent sequential overlapping segments of the analyte amino acid sequence. Such a preferred oligopeptide will generally have no more than one cysteine residue.

The invention further embraces a kit and a method for performing a fluorescence polarization assay. The kit includes a monoclonal antibody to an analyte, and an oligopeptide which competes with the analyte for binding to the monoclonal antibody and having an amino acid sequence which is configured to be incapable of formation of an internal disulfide bridge. In a highly preferred embodiment, the oligopeptide is tagged with a fluorophore and the labelled oligopeptide exhibits an increase in fluorescence upon binding to the antibody. In one embodiment, the oligopeptide has a binding affinity for the monoclonal antibody of between about 1/100 and 1/1000 of the binding affinity of the analyte for the monoclonal antibody.

The kit may further include a buffer suitable for making a solution containing the monoclonal antibody with the oligopeptide. In a further embodiment, the kit is packaged with instructions directing a user to prepare an assay solution containing the monoclonal antibody in a concentration of between about $1 \times 10^{-8}$ M and $1 \times 10^{-7}$ M and the oligopeptide in a concentration of between about $1 \times 10^{-9}$ M and about $1 \times 10^{-8}$ M.

In an alternate embodiment, the kit provides the monoclonal antibody and the labelled oligopeptide in an assay solution, with the ratio of oligopeptide to antibody being between about 1:1 and about 1:10. In a further embodiment, the assay solution contains the monoclonal antibody in a concentration of between about $1 \times 10^{-7}$ M and $1 \times 10^{-10}$ M and the oligopeptide is present in a concentration of between about $1 \times 10^{-7}$ M and about $1 \times 10^{-10}$ M. In another preferred embodiment, the monoclonal antibody concentration is between about $10^{-7}$ molar and $10^{-8}$ molar, while the oligopeptide concentration is between about $10^{-8}$ M and about $10^{-9}$ M.

A process for a fluorescence polarization immunoassay comprises the steps of: providing a monoclonal antibody which selectively binds an analyte; providing an oligopeptide constructed to selectively bind to the monoclonal antibody, and having an attached fluorescent molecule, the oligopeptide being one of the embodiments described herein; an internal disulfide bridge; contacting the monoclonal antibody with the oligopeptide in solution and determining a first polarization value of the fluorescent molecule; providing a sample comprising an unknown quantity of the analyte; adding the sample to the solution containing the monoclonal antibody and the oligopeptide and determining a second polarization value of the fluorescent molecule; and comparing the first and second polarization values to make an estimate of the amount of the analyte in the sample.

In a further embodiment, in the step of contacting the monoclonal antibody and the oligopeptide the ratio of oligopeptide to antibody is between about 1:1 and about 1:10.

In a highly preferred embodiment, quantitation of analyte in the sample is achievable for samples having concentrations of analyte between about $1 \times 10^{-7}$ molar and about $1 \times 10^{-10}$ molar.

A screening procedure for the oligopeptide composition includes a test for antibody binding affinity, with the oligopeptide having the highest binding affinity for a monoclonal antibody selectively reactive with the chosen analyte being preferred. The screening procedure may additionally include comparison of the content of proline residues, comparison of the degree of enhancement of fluorescence, and comparison of fluorescence polarization of bound fluorescently-labelled oligopeptide. Generally, each oligopeptide in the series comprises six to ten amino acid residues. One or more oligopeptides having relatively high binding affinities toward the antibody are selected for labelling with a fluorescent molecule. Measurements are made to determine which of the oligopeptide exhibit enhancement of fluorescence of the coupled fluorophore on binding of the oligopeptide to the antibody. Desirably, the oligopeptide is selected both to have a high binding affinity for the antibody, and to provide significant enhancement of fluorescence.

Preferably, the fluorescent label is a dye whose fluorescence occurs at a wavelength providing easy discrimination from the fluorescence of serum which occurs at about 500–515 nanometers (nm). Also desirably, the label is coupled to a side chain near the carboxyl end of the oligopeptide, for example via a free thiol of a cysteine residue.

The invention is exemplified with an oligopeptide and kit designed for an assay for the analyte human chorionic gonadotrophin, but the teachings are readily generalizable to other high molecular weight analytes.

BRIEF DESCRIPTION OF THE DRAWINGS

In the drawings, which depict what is presently regarded as the best mode for carrying out the invention.

DETAILED DESCRIPTION OF THE ILLUSTRATED EMBODIMENTS

Figure 1:
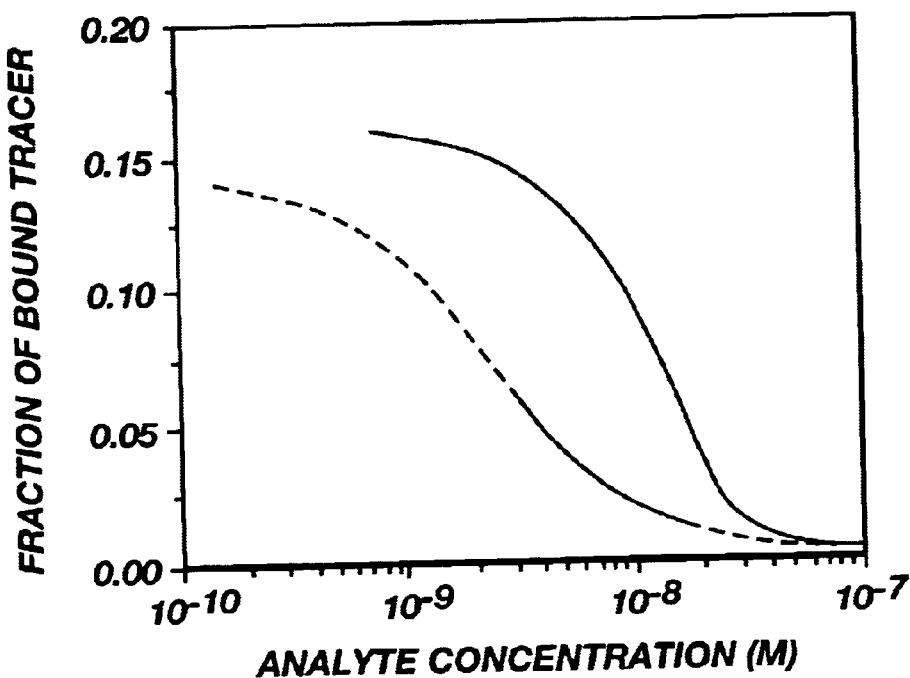
FIG. 1 is a graph of the fraction of bound tracer oligopeptide ($f_2$) versus analyte concentration ($L_1^o$) for $K_2=10^7$ M$^{-1}$ (solid line, $P_o=10^{-8}$ M) and $K_2=10^8$ M$^{-1}$ (dashed line, $P_o=10^{-9}$ M) and $K_1$ fixed at $10^9$ M$^{-1}$ showing the dependence of $f_2$ on $L_1^o$, and showing how increasing oligopeptide affinity helps to improve sensitivity and broaden dynamic range.

Beginning with the method of Geysen set forth in U.S. Pat. No. 4,833,092 and herein incorporated by reference, an oligopeptide capable of binding to an antibody raised against an analyte antigen is identified. The method entails synthesizing overlapping oligopeptides of typically between six and ten amino acids that correspond to the linear amino acid sequence of the analyte antigen. For example, if the analyte antigen contains 237 amino acid residues, 221 octapeptides would be synthesized, each differing from the adjacent octapeptides synthesized for the region by one additional residue at the C terminus and one missing residue at the N terminus. This is shown below for a hypothetical antigen having 12 amino acid residues, and using oligopeptides of eight amino acid residues.

```
Protein:  Ser-Gly-Asp-Gly-Lys-Cys-Ser-Arg-Leu-Pro-Thr-Gly    (SEQ ID #4)
Pep-1:    Ser-Gly-Asp-Gly-Lys-Cys-Ser-Arg                    (SEQ ID #5)
Pep-2:        Gly-Asp-Gly-Lys-Cys-Ser-Arg-Leu                (SEQ ID #6)
Pep-3:            Asp-Gly-Lys-Cys-Ser-Arg-Leu-Pro            (SEQ ID #7)
Pep-4:                Gly-Lys-Cys-Ser-Arg-Leu-Pro-Thr        (SEQ ID #8)
Pep-5:                    Lys-Cys-Ser-Arg-Leu-Pro-Thr-Gly    (SEQ ID #9)
```

In this example, the entire sequence of the antigen is here synthesized in multiple octapeptide pieces.

A panel containing a plurality of such overlapping oligopeptides, derived from at least a large region of the analyte amino acid sequence, are then individually screened against an antibody raised against the analyte antigen. The screening determines their respective binding affinities and specificity toward the antibody. Although several screening methods may be employed, a preferred method is the standard enzyme linked immuno-sorbent assay (ELISA) procedure. The ELISA procedure is well-known and will not be discussed in detail here.

Preferably, only one or two oligopeptides from the panel are found to bind strongly to the antibody. If larger numbers of different oligopeptides bind significantly to the antibody, this may be an indication that the binding is non-specific. In such a case, either a different antibody should be substituted for use in an FPI assay with the analyte, and the panel screened against the "new" antibody, or an oligopeptide panel derived from another region of the analyte should be screened in an attempt to meet this criterion.

In a preferred embodiment, several amino acid residues not part of the selected oligopeptide sequence are added at each end of the oligopeptide. The addition of these nonessential amino acids allows the conjugation of a fluorophore (fluorescent dye) to the oligopeptide without compromising its binding properties, and enables the fluorophore to be attached at some distance from the binding sequence. This construction also enables static fluorescence enhancement resulting from conformational changes upon binding of the tracer oligopeptide to the antibody. These conformational changes lead to an increased average fluorescent lifetime of the excited state, which in turn produces an increased fluorescence quantum yield. The increased quantum yield thereby increases the sensitivity of detection of anisotropy, since measured anisotropy is proportional to the fraction of fluorescence intensity due to the bound species. Higher $\Delta A$ values between the bound and free forms of the tracer oligopeptide contribute significantly to sensitivity as will be described subsequently in more detail.

In a preferred embodiment, the oligopeptides which in the initial screening are found to bind most strongly with the antibody, are labelled with a fluorescent dye and further tested for fluorescence enhancement and anisotropy (a measure of polarization). In a highly preferred embodiment, the selected fluorescently-labelled oligopeptide exhibits fluorescence enhancement, as opposed to fluorescence quenching, upon binding to the antibody under conditions of an FPI assay.

Fluorescence enhancement (Q) is defined as:

$$Q = (I - I_o)/I_o \quad (1)$$

where:

I is the fluorescence intensities of the antibody-antigen mixture, and $I_o$ is the fluorescence intensities of totally free antigen Equation (1) also defines fluorescence quenching in which case the sign of Q is negative. Since total fluorescence intensity is the weighted sum of contributions from bound and free labeled oligopeptide, the binding constant ($K_a$) for the oligopeptide to the antibody is related to Q by Equation (2):

$$2P_o = [K_a^{-1} Q/(Q_m - Q)] + L_o Q/Q_m \quad (2)$$

where:

$P_o$ is the total antibody concentration $Q_m$ is the maximal fluorescent enhancement, and $L_o$ is the total antigen (oligopeptide) concentration Equation (2) may be derived from the basic mass law of binding equilibrium, general procedures for which may be found in Herron, J. N., *Fluorescein Hapten: An Immunological Probe*; E. W. Voss, Jr. Ed.; CRC Press: Boca Raton, 1981; pp. 53–55, and *Fluorescence Spectroscopy. An Introduction for Biology and Medicine*; Pesce, A. J.; Rosen, C. G.; Pasby, T. L., Eds.; Marcel Dekker: New York, 1971; pp. 203–239. The fluorescence enhancement (Q) of a sample (relative to a reference) containing a labeled oligopeptide may be calculated as a function of the amount of antibody ($P_o$) added. Nonlinear regression of Q versus $P_o$ data may then be used to determine the values of $K_a$ and $Q_m$ according to Equation (2).

A method to measure the fluorescence anisotropy is as follows. Anisotropy is a parameter that is inter-related to fluorescence polarization and describes the same phenomenon. However, anisotropy is used in calculation of mole fraction or fluorescence fraction of bound tracers because it is additive with respect to these parameters while polarization is not. Anisotropy is used instead of polarization in calculating the antibody-antigen binding constant because the denominator in the anisotropy definition is the total fluorescent intensity. The fraction of fluorescence intensity ($F_b$) due to the bound form of oligopeptide is given by:

$$F_b=(A-A_f)/(A_b-A_f) \quad (3)$$

where:

A is the anisotropy value of the sample $A_b$ is the anisotropy value of totally-bound antigen, and $A_f$ is the anisotropy value of totally-free antigen In cases where both the bound and free fluorophores have the same level of fluorescence intensity, the mole fraction of bound oligopeptide ($f_b$) is the same as $F_b$. However, if the bound oligopeptide has higher intensity than the free oligopeptide, Equation (4) may be used to obtain $f_b$:

$$f_b=F_b/[1+Q_m(1-F_b)] \quad (4)$$

where:

$Q_m$ is determined from the intensity measurement

The binding constant $K_a$ may then be obtained by non-linear regression of $f_b$ versus $P_o$ according to Equation (5):

$$2P_o=L_o f_b + f_b K_a^{-1}/(1-f_b) \quad (5)$$

The above analysis, rather than the traditional Scatchard plot, is preferred because the latter approach is thought to violate the assumption of the least-squares method. Also, the linearized variables used in Scatchard analysis tend to have higher uncertainties due to error propagation than directly-measured variables (e.g. $P_o$, Q, $L_o$).

Figure 5:
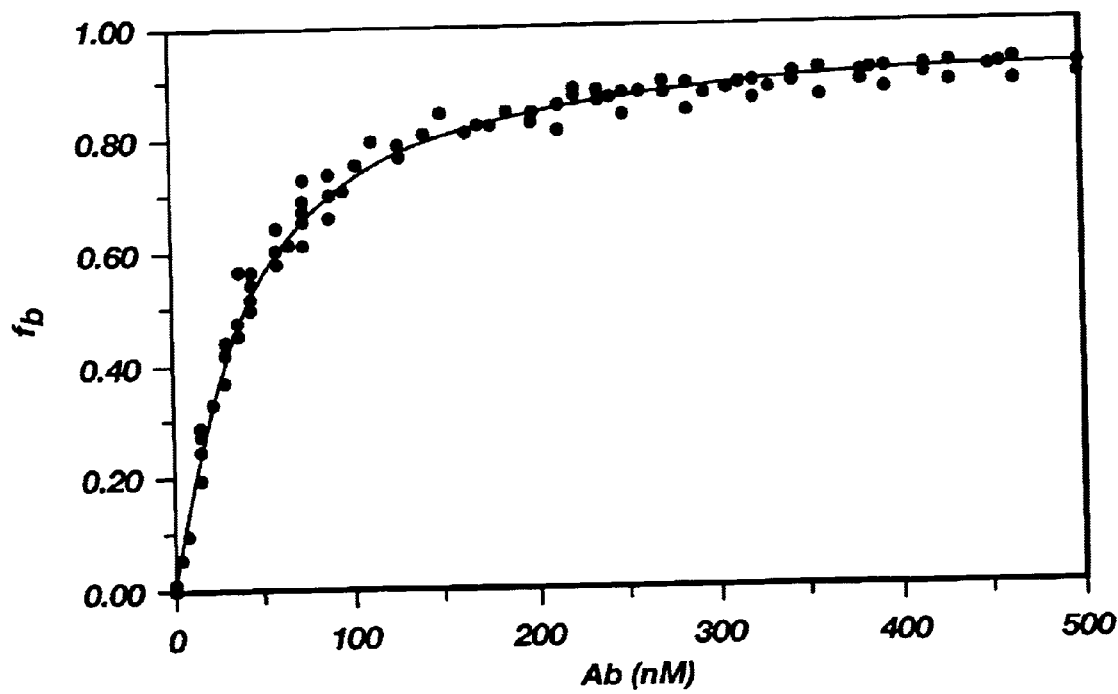
FIG. 5 is a graph of anisotropy (A) versus the mole fraction of bound tracer ($f_b$) for ten different $Q_m$ values, −0.999, −0.9, −0.7, −0.5, −0.3, 0, 1, 5, 50, and 500) read sequentially in the direction of the arrow starting from the lower right corner, and where the straight line in the middle is for no change in fluorescence intensity upon binding.

The relationship of anisotropy and $f_b$ for different values of $Q_m$ may be calculated according to Equations (3) and (4), and is shown in FIG. 5. Results indicate that the value of anisotropy is more sensitive to changes in $f_b$ when $Q_m$ is positive (e.g., when fluorescence is enhanced by binding to the antibody) in the region of small $f_b$. This is because the bound species exhibits a higher quantum yield that the unbound species, which allows preferential measurement of the former. Since most practical assays tend to operate at low $f_b$ values to gain sensitivity, this phenomenon helps to further enhance the assay sensitivity and accuracy. A labelled oligopeptide which exhibits fluorescence quenching, on the other hand, should be avoided since the measured anisotropy is less sensitive to changes in $f_b$. This is particularly so when quenching is significant (e.g. $Q_m=-90\%$ in FIG. 5).

Although the methods for determination of fluorescence enhancement and anisotropy described in the preceding paragraphs are preferred methods, it will be recognized by those of ordinary skill that other methods exist for determining the binding constant $K_a$ without departing from the scope of the invention.

From the above types of data, it is also possible to obtain the affinity constants of both analyte antigen and tracer oligopeptide with the antibody. Assuming the analyte antigen and the tracer oligopeptide bind to the same antibody with affinity constants of $K_1$ and $K_2$ respectively, the total analyte concentration ($L_1^o$) and the fraction of bound tracer ($f_2$) can be shown to follow the relationship in Equation (6):

$$L_1^o=[1+K_2(1-f_2)/K_1 f_2]\cdot[2P_o-(K_2^{-1}-f_2)/(1-f_2)-L_2^o f_2] \quad (6)$$

where $P_o$ is the concentration of antibody, and $L_2^o$ is the concentration of tracer oligopeptide Values of $f_2$ may be calculated according to Equations (3) and (4). A plot of mole fraction of bound tracer ($f_2$) as a function of analyte antigen concentration ($L_1^o$), followed by non-linear curve fitting according to Equation (6) yields values for $K_1$ and $K_2$.

EXAMPLE I

An oligopeptide capable of competing with hCG (human chorionic gonadotrophin) for binding to an anti-hCG antibody was identified by screening a panel 221 overlapping octapeptides against anti-hCG generally by the method of Geysen et al., and as described in the related copending application Ser. No. 08/096,338, the contents of which are hereby incorporated by reference. The oligopeptide length was selected to be an octapeptide; however, a panel of oligopeptides of a different length, from six to twelve residues, could also have been selected for screening. Human chorionic gonadotrophin has two chains and a total of 237 amino acid residues, for which a total of 221 octapeptides is required to provide an overlapping span of the entire sequences of the two hCG subunits. The octapeptides were synthesized by standard Fmoc methods and screened for specific binding to an anti-hCG-A antibody using ELISA procedures.

Of the 221 octapeptides tested, two octapeptides, SRLPGPSD (SEQ. ID #1) and RLPGPSDT (SEQ. ID #2) (both located in the carboxyl end of the hCG β chain), reacted strongly with the anti-hCG Mab. There was no significant reaction with other octapeptides. This result suggests that this antibody recognizes a single linear oligopeptide, with a core sequence of RLPGPS. In order to conjugate fluorescent dyes to this oligopeptide without compromising its binding properties, the following 13 residue sequence was synthesized: GSGSRLPGPSDTC (SEQ. ID #3).

The selected oligopeptide was synthesized in quantity according to the above sequence on an Applied Biosystems automated oligopeptide synthesizer, using the Fmoc methodology described in *Solid Phase Peptide Synthesis*; 2nd ed.; Stewart, J. M.; Young, J. D., Eds.; Pierce: Rockford, Ill., 1984. The crude oligopeptide was purified by reversed phase HPLC (high-pressure liquid chromatography) to >98% purity. Amino acid analysis and fast atom bombardment (FAB) mass spectroscopy were used to confirm the chemical structure.

The selected oligopeptide was fluorescently labelled and tested for fluorescence enhancement and polarization. The 5-isomer of a maleimide derivative of tetramethylrhodamine was purified from a commercially available mixture of 5- and 6-isomers (Molecular Probes, Eugene, Oreg.), using C-18 reversed phase FPLC (Pharmacia), and used to label the oligopeptide. A mixture of 0.1 mM oligopeptide and 0.15 mM dye was dissolved in 100 mM phosphate buffer (pH 6) and allowed to react for 24 hours at 4° C. After the incubation, the reaction mixture was separated on C-18 reversed phase FPLC. Good separation was achieved using a gradient of acetonitrile in water. The acetonitrile content was increased from 15% to 30% over a period of 20 minutes, followed by an isocratic elution at 30% acetonitrile. All solvents contained 0.1% trifluoroacetic acid. The oligopeptide-TMR conjugate eluted as a single peak at $\tau_R=32.8$ min., while hydrolyzed and nonreacted tetramethylrhodamine maleimide appeared at $\tau_R=60.0$ min. and $\tau_R=70.8$ min., respectively. This elution order may have been due to the hydrophilic nature of the oligopeptide, which contained only one nonpolar residue (Leu); a more hydrophobic oligopeptide might elute at a different time.

Fractions containing labelled oligopeptide were vacuum dried and analyzed by Fab mass spectroscopy. The concentration of the oligopeptide-TMR conjugate in solution was determined spectroscopically at 550 nm using an extinction coefficient ($\epsilon^m$) of 60,000 cm$^{-1}$M$^{-1}$. The molecular weight of oligopeptide-TMR conjugate was found to be 1715 daltons by Fab mass spectroscopy, in good agreement with the predicted value of 1714.88 daltons.

Fluorescence intensity and polarization measurements were made with a photon-counting spectrofluorometer (Model PC-1, ISS, Champaign, Ill.). An excitation wavelength of 543 nm (FWHH dispersion=4 nm) was used, and fluorescence emission was measured through a 570 nm long-pass filter. Fluorescence lifetimes were determined using a multifrequency phase and modulation fluorometer (Model K2, ISS). A $10^{-7}$ M solution of the hydroxylmaleimido derivative of tetramethylrhodamine was used as the reference lifetime ($\tau_{ref}$=2.964 ns). Samples were excited with the 514.5 nm line of a 30 W argon-ion laser (Spectra-Physics Model 2045). The modulation frequency was varied from 10 MHz to 200 MHz, a total of 15 frequencies were used. Frequency-dependent phase and modulation values were analyzed using the ISS decay analysis software package. All binding experiments were done at 6° C. In all titration experiments, the overall titrating volume added was kept below 4% of the total sample volume in cuvette. In all fluorescence measurements, background and noises were subtracted from total intensity readings.

EXAMPLE II

Measurement of fluorescence enhancement of labelled oligopeptide. A solution of oligopeptide-TMR at $4\times10^{-8}$ molar (M) was prepared and added to two cuvettes. One of these was titrated with 5 μl aliquots of antibody stock solution (sample), while the other was titrated with 5 μl aliquots of a mixture of mouse IgG and BSA in a 1:1 molar ratio (both purchased from Sigma Chemical Co., St. Louis, Mo.).

The purified monoclonal anti-hCG antibody was an anti-hCG-A antibody, and was a gift from Organon Technika, The Netherlands, and is characterized in greater detail in the related copending applications Ser. No. 08/096,338 now U.S. Pat. No. 6,482,651 and 08/071,579, now abandoned, the disclosures of which are hereby incorporated by reference. Antibody concentration was determined by absorption at 278 nm, using an extinction coefficient ($\epsilon_m^M$) of $1.03\times10^4$. The molar concentration of hCG was calculated from international units IU) using a specific activity of 12,100 IU/mg and molecular weight of 38 kD. All solutions were made in 100 mM sodium phosphate buffer, pH 7.4, unless otherwise indicated. The titration with mouse IgG and BSA was used to correct for nonspecific binding and instrument fluctuations. The fluorescence enhancement of the sample relative to the reference (Q) was calculated as a function of the amount of anti-hCG added ($P_o$) Nonlinear regression of Q versus $P_o$ data was used to determine the values of $K_a$ and $Q_m$ according to Equation 2. The fluorescence intensity of oligopeptide-TMR increased up to 20% upon binding.

Figure 3:
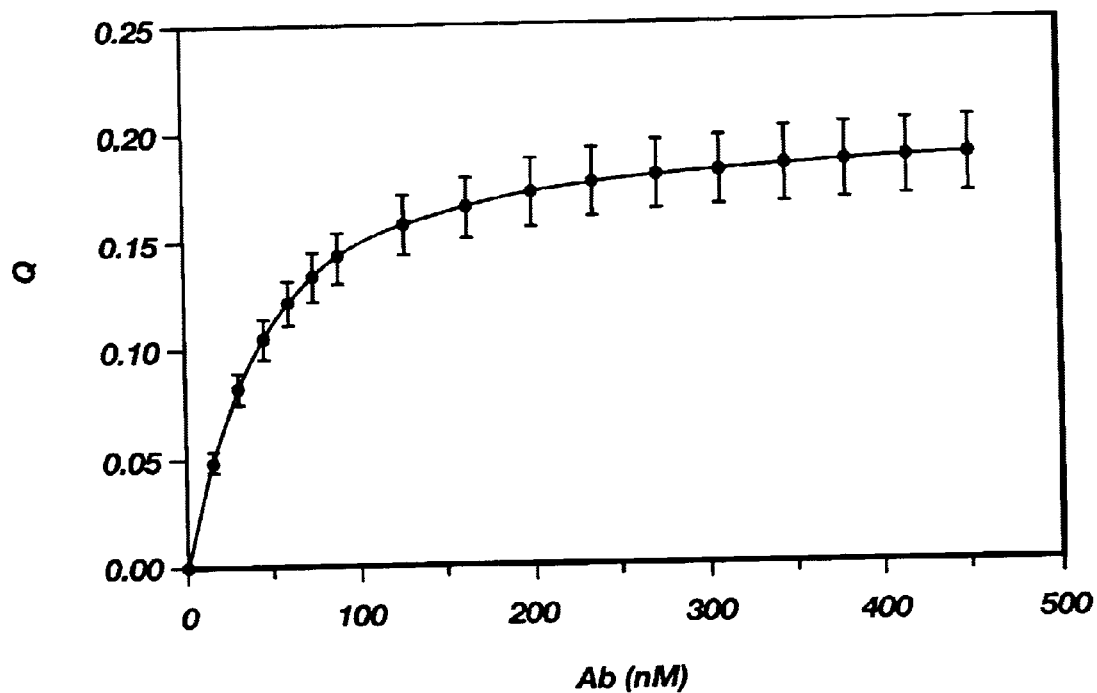
FIG. 3 is a graph of fluorescence enhancement (Q) as a function of antibody concentration.

FIG. 3 shows the change in enhancement factor (Q) as a function of antibody concentration. Values of 0.21, and $1.5\times10^7$ M$^{-1}$ were determined for the maximum enhancement ($Q_m$) and the binding constant ($K_a$) respectively, from the fluorescence enhancement measurements.

Figure 4:
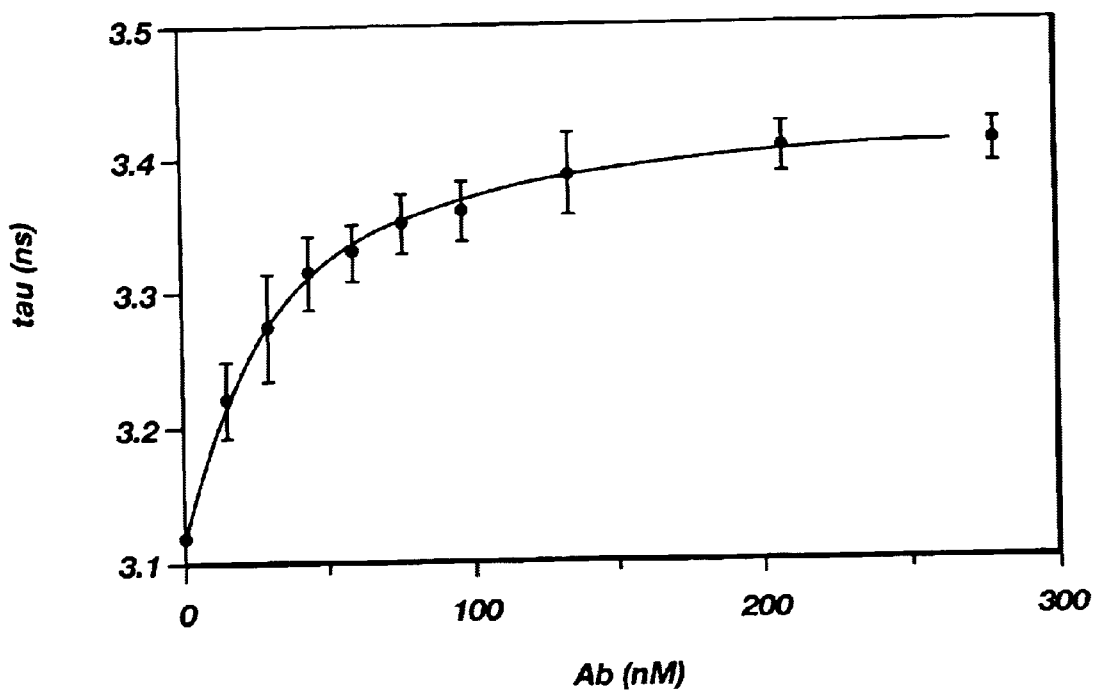
FIG. 4 is a graph of average fluorescence lifetime of labeled oligopeptide-TMR as a function of antibody concentration.

To elucidate the mechanism of fluorescence enhancement, fluorescence lifetimes were measured as a function of antibody concentration. As shown in FIG. 4, the average lifetime (as obtained by a one-component fit) changed from $\tau_o$=3.12 ns in the absence of antibody to a plateau value of $\tau_m$=3.44 ns; a 10.3% increase. Because the excited state lifetime is proportional to the fluorescence quantum yield, this result suggests that the prolonged lifetime accounts for about 50% of the increase in fluorescence intensity (dynamic enhancement). The other 50% change may have been due to the static enhancement resulting from conformational changes upon binding. In any case, it was found that the labelled selected oligopeptide exhibited fluorescence enhancement upon binding to the antibody.

EXAMPLE III

Figure 6A:
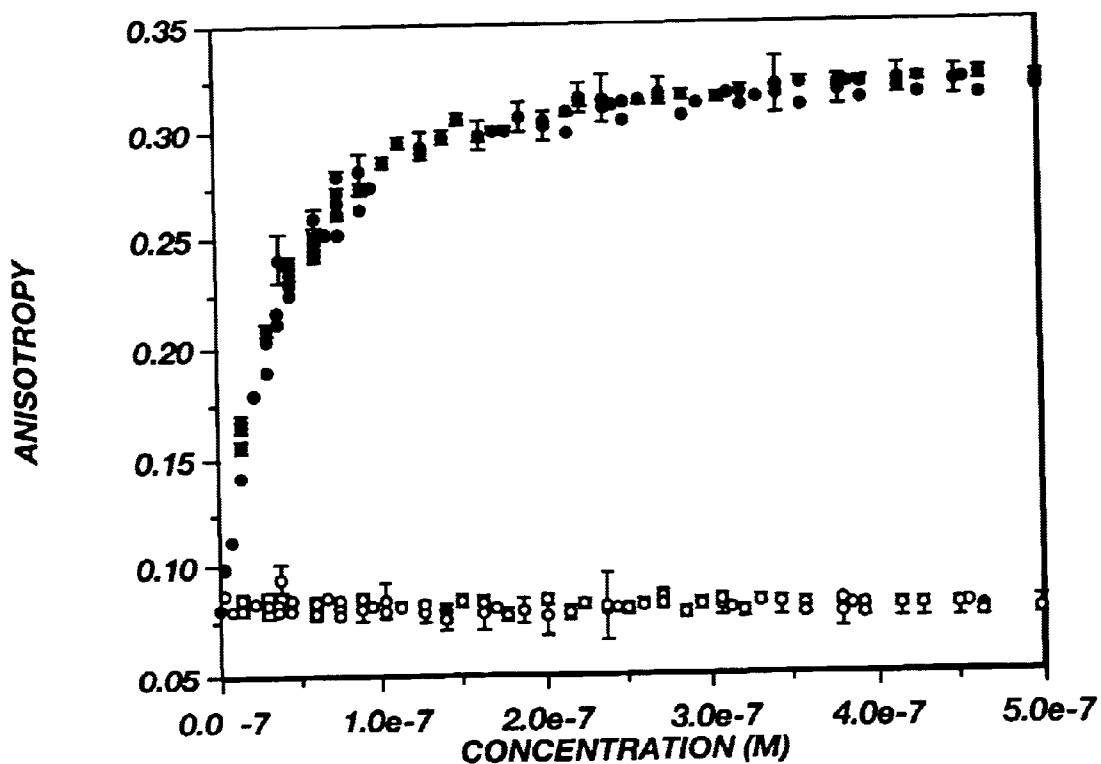
FIGS. 6A and 6B are graphs of fluorescence anisotropy of oligopeptide-TMR ($4\times10^{-8}$) as a function of antibody (filled squares) and BSA and IgG (open squares) concentrations.
Figure 6B:
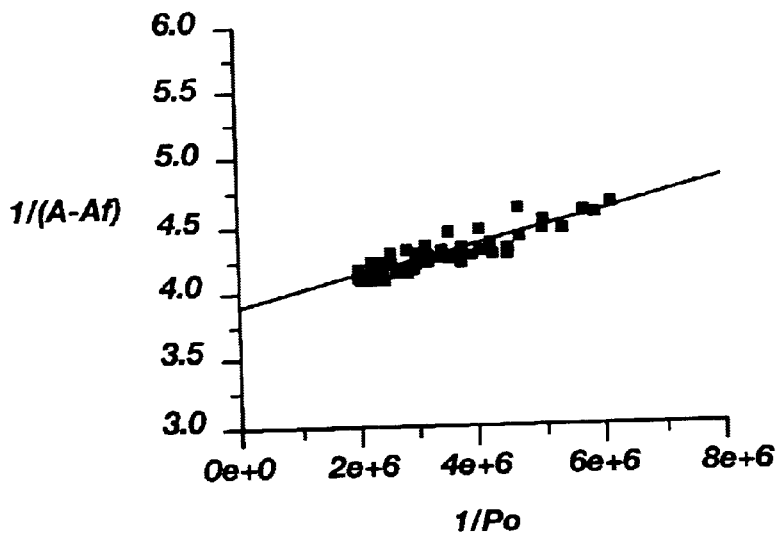

Measurement of fluorescence anisotropy of the oligopeptide. The titration was performed in a manner similar to that of EXAMPLE II. FIG. 6 shows the fluorescence anisotropy (A) as a function of antibody concentration ($P_o$) The anisotropy value in the absence of antibody ($A_f$) was 0.0830±0.0023 (N=100). Addition of anti-hCG resulted in a gradual increase in anisotropy. The anisotropy value for completely-bound oligopeptide-TMR ($A_b$) was 0.3402±0.0020 (N=48). This value was determined from a double-reciprocal plot of $1/(A-A_f)$ versus $1/P_o$ (FIG. 6B). The more than 4-fold increase in anisotropy is attributed to the large difference in size between the free oligopeptide (ca. 1700 daltons) and the oligopeptide-antibody complex (ca. 150,000 daltons). The fact that $A_b$ reaches 85% of the limiting anisotropy value of 0.4 indicates that the rotational mobility of the fluorophore is significantly hindered upon binding.

Figure 7:
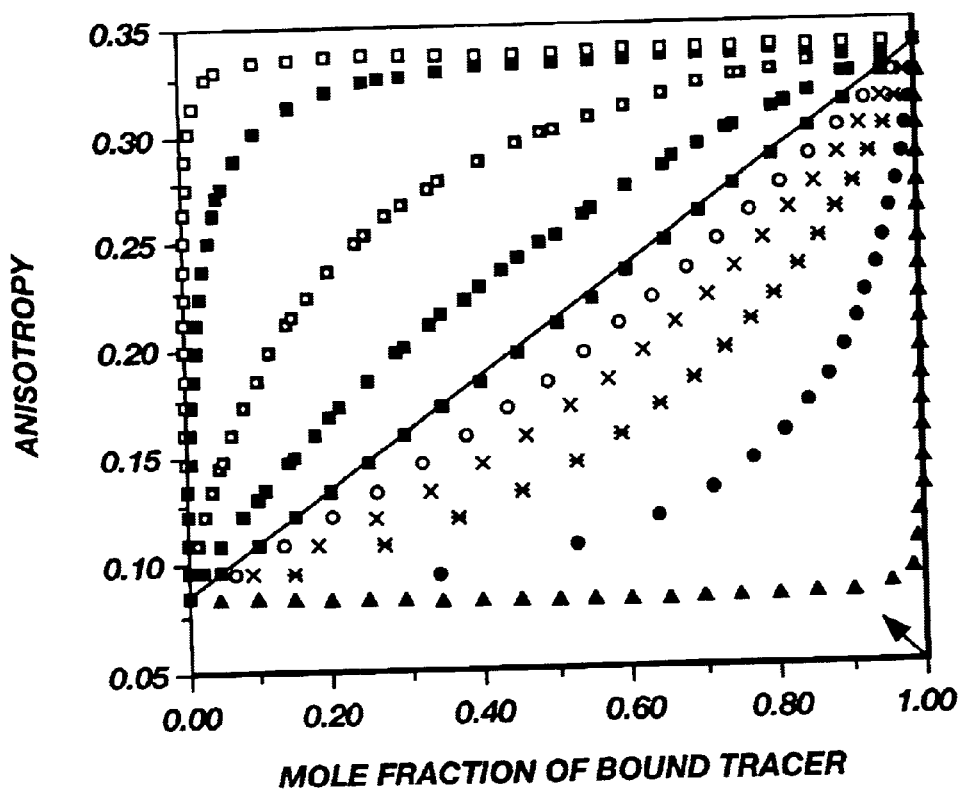
FIG. 7 is a graph of the mole fraction of bound oligopeptide ($f_b$) as a function of antibody concentration.

The above values of $A_f$ and $A_b$ were then used in conjunction with Equation (3) to calculate the fraction of fluorescence due to the bound species ($F_b$). This fraction was then corrected according to Equation (4) to obtain the mole fraction of the bound oligopeptide ($f_b$). A plot of $f_b$ vs. $P_o$ is illustrated in FIG. 7, and a binding constant ($K_a$) of $1.6\times10^7$ M$^{-1}$ was determined by non-linear regression of $f_b$ versus $P_o$ data according to Equation (5). This value is in excellent agreement with the $K_a$ value obtained from the intensity data.

A separate study (Van Erp, R.; Gribnau, T. C. J.; Sommeren, A. P. G. v.; Bloemers, H. P. J.: *J. Immunol. Methods* 140:235–241, 1991) regarding the binding of whole hCG to the same antibody resulted in a calculated value for $K_a$ of $4.8\times10^9$ M$^{-1}$ at 22° C. Thus, it appears that the binding affinity of the labelled oligopeptide for the monoclonal antibody in conjunction with which it is used in the FPI assay, is three hundred-fold lower than the binding affinity of hCG for the antibody.

Since the measured anisotropy (A) is proportional to the fraction of fluorescence intensity ($F_b$) due to the bound species, fluorescence enhancement upon binding gives higher A values for a given mole fraction of bound species ($f_b$) than in the absence of enhancement.

EXAMPLE IV

Binding specificity and reversibility are two critical factors for the usefulness of a new oligopeptide tracer. FIG. 6A shows that while the anisotropy of the oligopeptide increased from 0.083 to a plateau value of 0.34 upon specific binding to anti-hCG, titration of the oligopeptide with an identical amount of nonspecific mouse IgG and BSA did not produce any changes in anisotropy. This indicates that the binding is specific.

With respect to reversibility, the intact hCG molecule was used to displace the oligopeptide-TMR from the antibody. A mixture of oligopeptide-TMR ($4\times10^{-8}$ M) and anti-hCG ($2\times10^{-8}$ M) was first prepared. The starting anisotropy value was 0.1722±0.0037 (N=15), corresponding to about 30% bound oligopeptide, as expected with an affinity of $1.5\times10^{-7}$ M$^{-1}$. Under these conditions, the fraction of occupied binding sites (r) is also 30%. Displacement experiments were carried out by titrating the mixture with hCG.

Figure 8A:
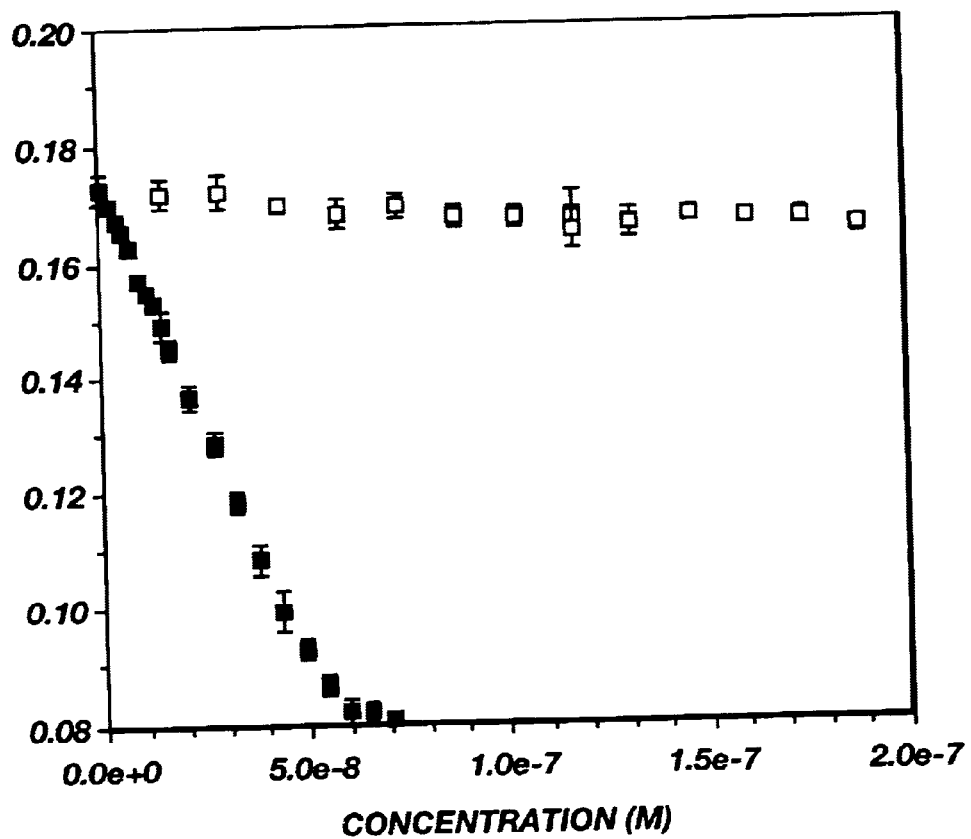
FIGS. 8A and 8B are graphs of the fluorescence anisotropy of oligopeptide-TMR as aliquots of hCG (filled squares) and BSA and IgG (open squares) were added to two identical mixtures of $2 \times 10^{-8}$ M antibody and $4 \times 10^{-8}$ M oligopeptide-TMR.

As shown in FIG. 8A, the anisotropy decreased gradually as the hCG concentration was increased, finally approaching that of free oligopeptide-TMR. If BSA and mouse IgG were used to titrate the sample, no depolarization was observed, indicating that displacement was specific to hCG. The experiment in FIG. 8A was also repeated in the presence of $3 \times 10^{-7}$ M BSA & IgG and identical results were obtained. This indicates that the binding of oligopeptide-TMR tracer with antibody is both specific and reversible.

Figure 8B:
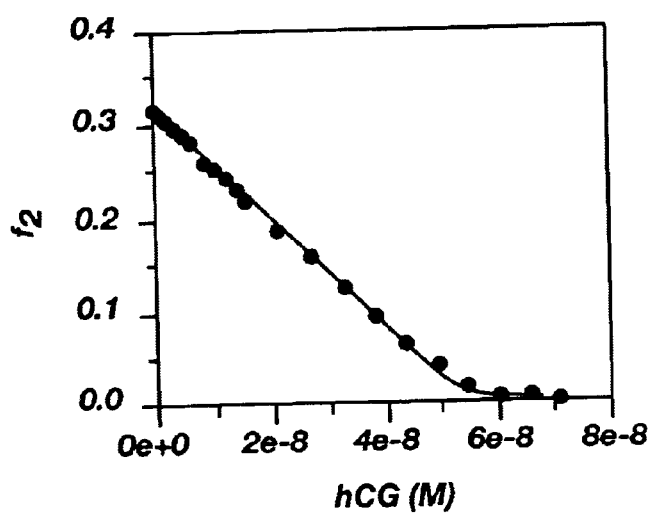

Using the data in FIG. 8A it was also possible to obtain the affinity constants of both hCG and oligopeptide-TMR with the antibody. Assuming that the hCG and the tracer oligopeptide bind to the antibody with affinity constants of $K_1$ and $K_2$, respectively, the total analyte concentration ($L_1^o$) and the fraction of bound tracer ($f_2$) can be shown to follow the relationship in Equation (6). Values of $f_2$ were calculated according to Equations (3) and (4). A plot of $f_2$ versus hCG concentration is shown in FIG. 8B.

Non-linear curve fitting of the data in FIG. 8A according to Equation (6) gave $K_1=9.4 \times 10^9$ M$^{-1}$ and $K_2=1.6 \times 10^7$ M$^{-1}$ for the tracer oligopeptide. This value of $K_2$ is in excellent agreement with those obtained from intensity and anisotropy measurements (FIGS. 3 and 6A). The value of $K_1$ is about two-fold higher than that reported by Van Erp et al. This discrepancy may be due to differences in temperatures.

A fluorescence polarization assay procedure begins with the provision of a fluorescently-labelled tracer oligopeptide as disclosed previously herein. A solution containing a mixture of labelled tracer oligopeptide bound to the antibody is prepared, and the initial polarization value is determined. As the solution is titrated with a solution containing the analyte antigen, the polarization value gradually decreases as the unlabeled analyte antigens displace the tracer oligopeptides from the antibody binding sites into solution. The change in polarization value is related to the concentration of analyte by a standard curve of polarization values as a function of known concentrations of analyte.

Desirably, the tracer oligopeptide provided for the FPI assay is much smaller in size than the analyte, but still able to compete effectively for binding to the antibody. The molecular weight of the oligopeptide should further be no more than $\frac{1}{100}$, and preferably at least about $\frac{1}{500}$ to $\frac{1}{1000}$, of the molecular weight of the antibody, to ensure a substantial difference in polarization of fluorescence between the free tracer oligopeptide and the antibody-bound tracer oligopeptide. Also desirably, the antibody provided for the assay has the property of binding only to a single linear oligopeptide sequence.

In a preferred embodiment of the assay process, the oligopeptide tracer is selected to exhibit fluorescence enhancement of the fluorescence of the label upon binding to the antibody. This is especially desirable in a further embodiment in which low $f_b$ values are used to gain sensitivity.

In another preferred embodiment, the fluorophore with which the oligopeptide is labelled is selected to have excitation and emission wavelength ranges which do not significantly overlap with serum fluorescence at 500–515 nm. Fluorophores selected from the group including tetramethylrhodamine and the cyanine dyes, meet this criterion.

Figure 2:
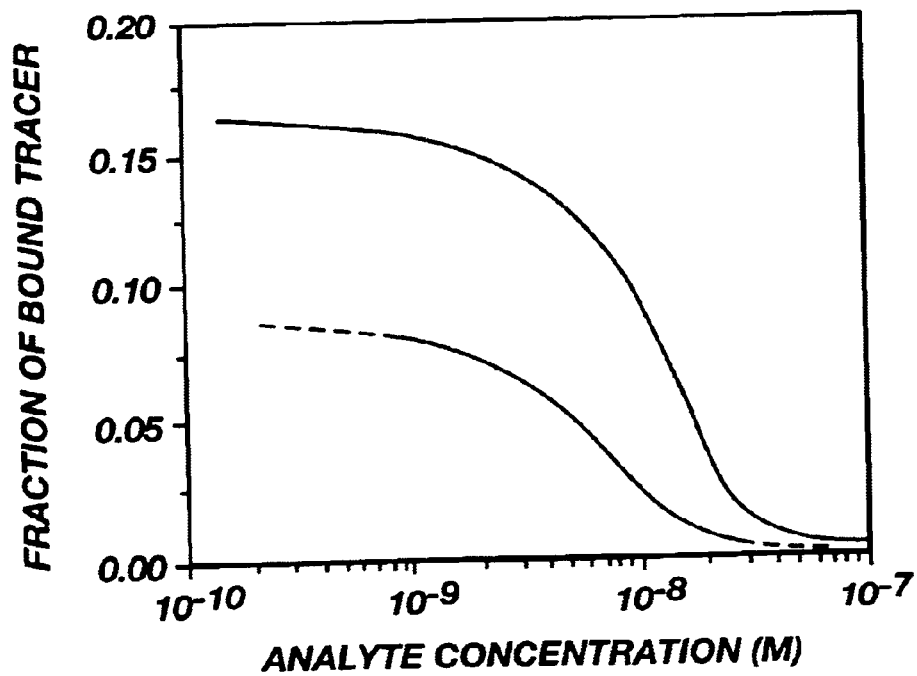
FIG. 2 is a graph of the fraction of bound tracer oligopeptide ($f_2$) versus analyte concentration ($L_1^o$) for $P_o=5\times10^{-8}$ (solid line) and $P_o=5-10^{-9}$ (dashed line) with $K_1$, $K_2$, and $L_2^o$ fixed showing how reducing antibody concentration helps to improve sensitivity, but degrades signal-to-noise ratio.

Additionally, a preferred embodiment of the process provides for desired respective concentration ranges and ratios of antibody to oligopeptide. FIG. 2 shows the dependence of $f_2$ on $L_1^o$ for two different values of $P_o$ ($5 \times 10^{-9}$ and $10^{-8}$ M)

with $K_1$, $K_2$, and $L_2^o$ held constant ($K_1=10^9$ M, $K_2=10^7$ M, and $L_2^o=2 \times 10^{-9}$ M). At higher antibody concentration, the value of $f_2$ varies from 0 to 0.16, while at lower antibody concentration, $f_2$ varies from 0 to 0.08. Thus, it can be seen that decreasing the antibody concentration by half can increase sensitivity by a factor of two. However, the gain in sensitivity is achieved at the expense of the signal-to-noise ratio. Thus, optimization is a trade-off to be determined for each individual antibody-oligopeptide-analyte system.

The brightness of the fluorescent label used also affects the sensitivity of the assay. Antibody affinity is a critical factor influencing FPI assay sensitivity. If the antibody binds the analyte or oligopeptide with 10-fold higher affinity, the curves in FIGS. 1 and 2 would shift one log unit to the left, resulting in a 10-fold increase in sensitivity. To realize this increase, the concentrations of antibody and tracer will also have to be reduced 10-fold as required by the binding equation. Under the condition of low tracer concentration, the choice of fluorescent label becomes critical. Use of a brighter fluorophore would allow for lower detection limits and give better signal-to-noise ratio. Fluorescent dyes from the fluorescein family (e.g., fluorescein, tetramethylrhodamine, Texas Red™, etc.) have relatively high extinction coefficients (60,000–100,000 M$^{-1}$cm$^{-1}$) and fluorescence quantum yields greater than 85%. They are the most commonly used labels. Another group of dyes useful in the assay are cyanine compounds. These possess similar desirable properties and are commercially available (Cy3 and Cy5). They have an extinction coefficient of 200,000 M$^{-1}$ cm$^{-1}$ and a quantum yield of 28% when conjugated to immunoglobulins. Also, because cyanine dyes can be excited at a wavelength region between 630 nm and 650 nm, inexpensive lasers and semiconductor laser diodes may be used for excitation and fluorescence detection. This provides the possibility of great improvements in expense of equipment for performance of the FPI assay.

Thus, the ability to attach any dye including fluorescein, tetramethylrhodamine, Texas Red, and cyanine compounds to the oligopeptide by means of the added tail segments, easily and without disrupting the antibody binding properties of the oligopeptide, is a prominent advantage of the present composition and assay process.

Additionally, the relative amounts of oligopeptide to analyte affect the sensitivity of the assay. Thus, the assay is desirably designed to use a concentration of oligopeptide which provides good sensitivity in the concentration range of analyte whose detection is desired. Also, the standard curve from which the raw measurements are converted to estimates of analyte concentration, should be made under concentration ranges and ratios and with analyte standard concentrations, similar to those of the assay itself.

EXAMPLE V

In this example, a sample containing the high molecular weight antigen human chorionic gonadotrophin (hCG) was assayed according to the disclosed procedure. Highly purified hCG (550 IU/vial) was a gift of Organon Technika, The Netherlands. Measurements of fluorescence intensity, polarization, and excited-state lifetime were used to study the binding of the tracer oligopeptide with the antibody in the absence and presence of the competing hCG and to characterize the binding mechanism.

Figure 9:
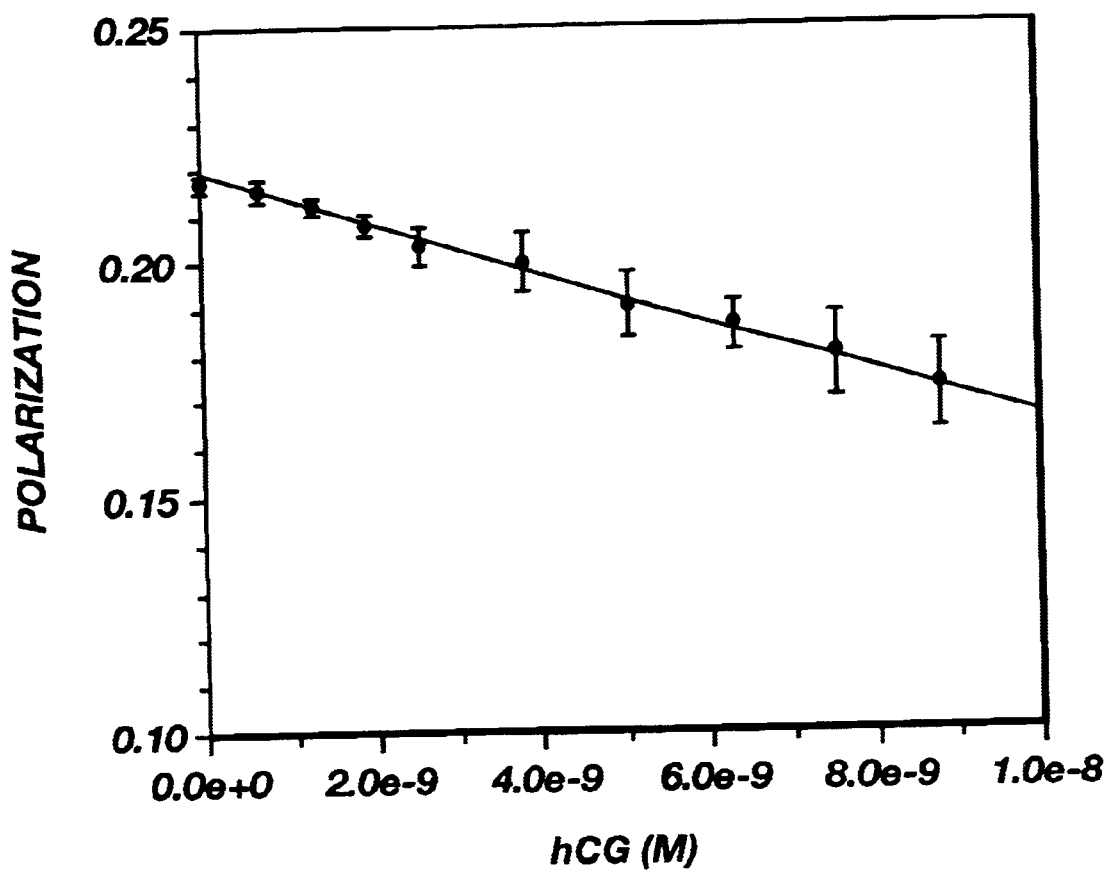
FIG. 9 is a graph of polarization values versus concentration of hCG for use as a calibration curve.

FIG. 9 is a standard curve of an FPIA assay in which a mixture of $1.5 \times 10^{-8}$ M antibody and $4 \times 10^{-9}$ M tracer oligopeptide was titrated by aliquots of hCG stock solution. A 95% confidence limit was used in determining the lowest hCG level ($L_{min}$) that could be detected with this particular embodiment of the assay. Specifically, $L_{min}$ was defined as the hCG concentration which corresponds to 1.96 times the standard deviation of the polarization value obtained in the absence of hCG. In this case, $L_{min}$ was found to be $1 \times 10^{-9}$ M (N=3), i.e., 0.46 IU/ml. This level of sensitivity allows the detection of serum hCG between 30 and 40 days post-conception (typically; 30 days, >100 mIU/ml; 40 days, >2000 mIU/mi). If higher hCG levels are expected, as in the case of ectopic pregnancy and moles, the system can easily be adjusted to operate in a higher detection range by properly formulating the antibody and tracer concentrations. However, if lower detection limit of hCG is desired, e.g., early diagnosis of hCG-producing tumors, several parameters must be modified as discussed below.

A common concern with fluorescence assays is the interference from serum fluorescence at 500–515 nm. Because tetramethylrhodamine has absorption and emission maxima at 550 nm and 580 nm, respectively, such interference is substantially avoided.

A further notable point is that, taken together with the data indicating that the binding affinity of hCG for the antibody is at least 300-fold to over 500-fold higher than is the binding affinity of the oligopeptide, the results presented in EXAMPLE V demonstrate that an oligopeptide constructed and selected according to the disclosed procedures is highly useful in the FPI assay even when its binding affinity is much lower than that of the analyte.

In cases where $f_2$ needs to be very low, fluorescence enhancement is highly desired because it can effectively increase the $\Delta A$ value. (see FIG. 5).

It is within contemplation to achieve further improvements in sensitivity of the assay. For example, if the oligopeptide affinity ($K_2$) is increased by a factor of 10, the sensitivity will correspondingly increase ten-fold, and the detection range becomes broader. This result is shown in FIG. 1 for simulation curves of $f_2$ versus $L_1^\circ$ for two different $K_2$ (tracer oligopeptide affinity constant) values ($10^7$ and $10^8$ $M^{-1}$). Also, because the fraction of bound tracer and actual tracer concentration ($L_2^\circ$) is held constant in both cases, the sensitivity is improved without affecting signal-to-noise ratio. A 10-fold increase in the oligopeptide affinity would allow measurement of hCG levels below 50 mIU/ml (108 picomolar).

Currently, there are two practical ways to increase oligopeptide binding affinities. In one approach, the oligopeptide selected as described is used as a starting template for systematic substitution of both D- and L-amino acids at key positions to attempt to construct an oligopeptide with a higher binding affinity. In a more traditional approach, an oligopeptide library of over 200 million oligopeptides is searched for a more strongly-binding oligopeptide.

The composition and method described hereinabove provide rapid determination of an analyte in the nanomolar concentration range and with negligible interference due to nonspecific binding. The use of tetramethylrhodamine or cyanine dyes as the fluorescent label eliminates interference from serum fluorescence. Sub-nanomolar sensitivity is primarily limited by the binding affinities of the antibody to both hCG and the oligopeptide. Fluorescence enhancement upon binding is also an important factor in designing FPIAs of high sensitivity.

While the composition and assay process have been described and characterized using hCG as an example, the teachings of the invention would be readily applied by one of ordinary skill to the design of fluorescence polarization assays of other high molecular weight analytes. The scope of the invention is thus not limited to the disclosed example, and is defined solely by the claims.

What is claimed is:

1. A process for performing a fluorescence polarization immunoassay, said process comprising:

providing a monoclonal antibody having an analyte-binding site which selectively binds an analyte;

providing an oligopeptide tracer comprising an oligopeptide, said oligopeptide having an amino acid sequence which does not form internal disulfide bridges, and which is constructed to selectively bind to the analyte-binding site, and having an N-terminal end, a linker segment of from one to five amino acid residues covalently linked to the N-terminal end of the oligopeptide, and a fluorescent moiety attached to the linker segment contacting the monoclonal antibody with the oligopeptide tracer in a solution and determining a first polarization value of the fluorescent molecule;

providing a sample comprising an unknown quantity of the analyte; adding the sample to the solution containing the monoclonal antibody and the oligopeptide tracer and determining a second polarization value of the fluorescent molecule; and comparing the first and second polarization values to make an estimate of the amount of the analyte in the sample.

2. The process of claim 1, wherein when providing an oligopeptide tracer further comprises:

screening a plurality of different peptides having amino acid sequences which define a series of overlapping segments of an amino acid sequence of the analyte, selecting one or more peptide antigens having high binding affinities for the monoclonal antibody, and determining which of the peptide antigens has the property of fluorescence enhancement upon binding to the monoclonal antibody.

3. The process of claim 2, wherein the analyte is human chorionic gonadotrophin.

4. The process of claim 1, wherein during the contact of the monoclonal antibody and the oligopeptide tracer, the monoclonal antibody is present at a concentration of between about $1 \times 10^{-8}$ M and $2 \times 10^{-8}$ M, and the oligopeptide is present in a concentration of between about $2 \times 10^{-9}$ M and about $8 \times 10^{-9}$ M.

5. The process of claim 1, wherein reproducible quantitation of analyte in the sample is achievable for samples having concentrations of analyte between about $1 \times 10^{-7}$ molar and about $1 \times 10^{-1}$ molar.

6. The process of claim 1, wherein the oligopeptide tracer has a binding affinity for the monoclonal antibody of between about $\frac{1}{10}$ and $\frac{1}{1000}$ of the binding affinity of the analyte for the monoclonal antibody.

7. A fluorescence polarization immunoassay kit, comprising:

a monoclonal antibody which selectively binds a selected analyte, and an oligopeptide tracer which competes with said selected analyte for binding to said monoclonal antibody, said oligopeptide tracer having an amino acid sequence which does not form internal disulfide bridges, and further having an epitope region to which has been added at the N-terminal end of the epitope region, from one to five additional amino acids, at the C-terminal end of the epitope region, two additional amino acids, and a fluorescent compound bound to at least one of said additional amino acids.

8. The fluorescence polarization immunoassay kit of claim 7, wherein said oligopeptide tracer and said monoclonal antibody are together in solution in a buffer suitable for a fluorescence polarization assay, and which kit further contains instructions for performing a fluorescence polarization assay using said monoclonal antibody at a concentration of between about $5 \times 10^{-7}$ molar and about $5 \times 10^{-8}$ molar, and said oligopeptide tracer at a concentration of between about $1 \times 10^{-9}$ molar and about $2 \times 10^{-8}$ molar.

9. The fluorescence polarization immunoassay kit of claim 8, wherein said oligopeptide tracer has a binding affinity for said monoclonal antibody which is between about $\frac{1}{10}$ and $\frac{1}{10,000}$ of the binding affinity of said selected analyte for said monoclonal antibody.

10. The fluorescence polarization immunoassay kit of claim 9, wherein the epitope region of the oligopeptide tracer has an amino acid sequence which is selected by screening a plurality of different oligopeptides having amino acid sequences which define a series of overlapping segments of an amino acid sequence of said selected analyte, and selecting from said plurality of oligopeptides, an oligopeptide having the highest binding affinity for said monoclonal antibody.

11. The fluorescence polarization immunoassay kit of claim 10, wherein said solution contains said monoclonal antibody in a concentration of between about $1 \times 10^{-8}$ M and $2 \times 10^{-8}$ M and said oligopeptide tracer in a concentration of between about $2 \times 10^{-9}$ M and about $8 \times 10^{-9}$ M.

12. The fluorescence polarization assay kit of claim 7, which is formulated to provide reproducible quantitation of analyte in a sample having said selected analyte at a concentration of between about $1 \times 10^{-8}$ molar and about $1 \times 10^{-10}$ molar.

13. The kit fluorescence polarization immunoassay of claim 12, wherein said monoclonal antibody is an antibody which selectively binds human chorionic gonadotrophin.

14. The fluorescence polarization immunoassay kit of claim 9, which is packaged with instructions directing a user to prepare an assay solution containing said monoclonal antibody at a concentration of between about $1 \times 10^{-8}$ M and $2 \times 10^{-8}$ M and said oligopeptide tracer in a concentration of between about $2 \times 10^{-9}$ M and about $8 \times 10^{-9}$ M.

15. The fluorescence polarization immunoassay kit of claim 14, wherein said oligopeptide tracer has a binding affinity for said monoclonal antibody of between about $1/10$ and $1/10000$ of the binding affinity of said selected analyte for said monoclonal antibody.

16. A fluorescence polarization immunoassay kit, comprising:

a monoclonal antibody which selectively binds a selected analyte, and an oligopeptide having an amino acid sequence which does not form internal disulfide bridges and which competes with said selected analyte for binding to said monoclonal antibody, said oligopeptide comprising an epitope region with opposing an epitope region with an N-terminal end and a C-terminal end, a first spacer segment of one to five amino acid residues attached to the N-terminal end of said epitope region, a second spacer segment of two amino acid residues attached to the C-terminal end of said epitope region, and a fluorescent compound bound to said at least one of either said first spacer segment or said second spacer segment.

17. The fluorescence polarization immunoassay kit of claim 16, wherein said oligopeptide has a lower affinity for said monoclonal antibody than said selected analyte, and wherein the fluorescence polarization immunoassay kit is constructed to permit detection of said analyte in samples wherein said analyte is present in initial concentrations of $10^{-9}$ to $10^{-10}$ molar.

18. A process for performing a fluorescence polarization immunoassay, said process comprising:

providing a monoclonal antibody which selectively binds an analyte;

providing an oligopeptide tracer comprising an oligopeptide, said oligopeptide having an amino acid sequence which does not form internal disulfide bridges, said oligopeptide further being constructed to selectively bind to the monoclonal antibody and to have an N-terminal end, a spacer segment of from one to five additional amino acids coupled to the N-terminal end of said oligopeptide, and a fluorescent moiety attached to the spacer segment;

contacting the monoclonal antibody with the oligopeptide tracer in solution and determining a first polarization value of the fluorescent molecule;

providing a sample comprising an unknown quantity of the analyte;

adding the sample to the solution containing the monoclonal antibody and the oligopeptide tracer and determining a second polarization value of the fluorescent molecule; and comparing the first and second polarization values to make an estimate of the amount of the analyte in the sample.

19. The process of claim 18, wherein the spacer segment includes two residues.

20. The process of claim 18, wherein said analyte is present in said sample at a concentration of $10^{-9}$ molar to $10^{-10}$ molar.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 8 amino acids
      (B) TYPE: amino acid
      (D) TOPOLOGY: linear (ii) MOLECULE TYPE: peptide (iii) HYPOTHETICAL: NO (v) FRAGMENT TYPE: internal (vi) ORIGINAL SOURCE:
      (A) ORGANISM: Homo sapiens sapiens (xi) SEQUENCE DESCRIPTION: SEQ ID NO:1:

Ser Arg Leu Pro Gly Pro Ser Asp
1             5

(2) INFORMATION FOR SEQ ID NO:2:

(i) SEQUENCE CHARACTERISTICS:
      (A) LENGTH: 8 amino acids (B) TYPE: amino acid
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: Homo sapiens sapiens (xi) SEQUENCE DESCRIPTION: SEQ ID NO:2:

Arg Leu Pro Gly Pro Ser Asp Thr
1               5

(2) INFORMATION FOR SEQ ID NO:3:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (iii) HYPOTHETICAL: YES (v) FRAGMENT TYPE: internal (vi) ORIGINAL SOURCE:
        (A) ORGANISM: Homo sapiens sapiens (xi) SEQUENCE DESCRIPTION: SEQ ID NO:3:

Gly Ser Gly Ser Arg Leu Pro Gly Pro Ser Asp Thr Cys
1               5                   10

(2) INFORMATION FOR SEQ ID NO:4:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (iii) HYPOTHETICAL: YES (v) FRAGMENT TYPE: internal (vi) ORIGINAL SOURCE:
        (A) ORGANISM: None (xi) SEQUENCE DESCRIPTION: SEQ ID NO:4:

Ser Gly Asp Gly Lys Cys Ser Arg Leu Pro Thr Gly
1               5                   10

(2) INFORMATION FOR SEQ ID NO:5:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (iii) HYPOTHETICAL: YES (v) FRAGMENT TYPE: internal (vi) ORIGINAL SOURCE:
        (A) ORGANISM: None (xi) SEQUENCE DESCRIPTION: SEQ ID NO:5:

```
Ser Gly Asp Gly Lys Cys Ser Arg
1               5
```

(2) INFORMATION FOR SEQ ID NO:6:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (iii) HYPOTHETICAL: YES (v) FRAGMENT TYPE: internal (vi) ORIGINAL SOURCE:
        (A) ORGANISM: None (xi) SEQUENCE DESCRIPTION: SEQ ID NO:6:

```
Gly Asp Gly Lys Cys Ser Arg Leu
1               5
```

(2) INFORMATION FOR SEQ ID NO:7:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (iii) HYPOTHETICAL: YES (v) FRAGMENT TYPE: internal (vi) ORIGINAL SOURCE:
        (A) ORGANISM: None (xi) SEQUENCE DESCRIPTION: SEQ ID NO:7:

```
Asp Gly Lys Cys Ser Arg Leu Pro
1               5
```

(2) INFORMATION FOR SEQ ID NO:8:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (iii) HYPOTHETICAL: YES (v) FRAGMENT TYPE: internal (vi) ORIGINAL SOURCE:
        (A) ORGANISM: None (xi) SEQUENCE DESCRIPTION: SEQ ID NO:8:

```
Gly Lys Cys Ser Arg Leu Pro Thr
1               5
```

(2) INFORMATION FOR SEQ ID NO:9:

(i) SEQUENCE CHARACTERISTICS:
        (A) LENGTH: 8 amino acids
        (B) TYPE: amino acid
        (D) TOPOLOGY: linear (ii) MOLECULE TYPE: peptide -continued

```
    (iii) HYPOTHETICAL: YES (v) FRAGMENT TYPE: internal (vi) ORIGINAL SOURCE:
         (A) ORGANISM: None (xi) SEQUENCE DESCRIPTION: SEQ ID NO:9:

Lys Cys Ser Arg Leu Pro Thr Gly
1               5
```